United States Patent [19]

Logan et al.

[11] Patent Number: 5,276,052
[45] Date of Patent: Jan. 4, 1994

[54] USE OF A BENZO[B]THIOPENE-2-CARBOXIMIDA-MIDE DERIVATIVE

[75] Inventors: Robert T. Logan, Lanark; James Redpath, Bishopbriggs; George McGarry, Airdrie; Robert G. Roy, Larkhall, all of Scotland

[73] Assignee: Akzo N.V., Velperweg, Netherlands

[21] Appl. No.: 32,759

[22] Filed: Mar. 16, 1993

Related U.S. Application Data

[63] Continuation of Ser. No. 779,688, Oct. 21, 1991, abandoned.

[30] Foreign Application Priority Data

Oct. 26, 1990 [EP] European Pat. Off. ......... 903117448

[51] Int. Cl.$^5$ .............................................. A61K 31/38
[52] U.S. Cl. ............................................................ 514/443
[58] Field of Search ........................ 514/443; 549/51

[56] References Cited

U.S. PATENT DOCUMENTS

| | | | |
|---|---|---|---|
| 3,398,161 | 8/1968 | Turner | 549/51 |
| 4,665,206 | 5/1987 | Redpath et al. | 549/51 |
| 4,705,782 | 11/1987 | Logan et al. | 514/150 |
| 4,929,636 | 5/1990 | Redpath et al. | 514/443 |
| 5,026,724 | 6/1991 | Logan et al. | 514/443 |

FOREIGN PATENT DOCUMENTS

| | | |
|---|---|---|
| 0026593 | 4/1981 | European Pat. Off. . |
| 0158380 | 10/1985 | European Pat. Off. . |
| 0352832 | 1/1990 | European Pat. Off. . |

OTHER PUBLICATIONS

Miller et al., British Journal of Pharmacology, vol. 100, No. 4 pp. 843-894 (1990).

*Pharmacological Basis of Therapeutics,* Goodman-Gilman et al., 7th Edition, pp. 5, 10 and 28, Macmillan & Co., New York (1985).

*Primary Examiner*—Frederick E. Waddell
*Assistant Examiner*—K. Weddington
*Attorney, Agent, or Firm*—William M. Blackstone

[57] ABSTRACT

The invention relates to the use of the benzo[b]-thiophene-2-carboximidamide derivative having formula I

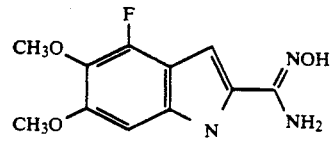

or pharmaceutically acceptable salts thereof, for the preparation of a medicament which is suitable for the treatment of heart failure, having high bioavailability without inducing nausea, vomiting and/or restlessness.

1 Claim, No Drawings

USE OF A BENZO[B]THIOPENE-2-CARBOXIMIDAMIDE DERIVATIVE

This is a continuation of application Ser. No. 07/779,688 filed Oct. 21, 1991; now abandoned.

The invention relates to the use of the benzo[b]-thiophene-2-carboximidamide derivative having formula I

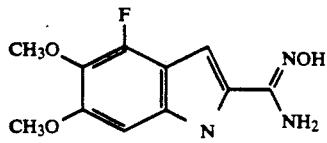

or pharmaceutically acceptable salts thereof, for the preparation of a medicament which is suitable for the treatment of heart failure, having high bioavailability without inducing nausea, vomiting and/or restlessness.

The benzo[b]thiophene-2-carboximidamide derivative having formula I was disclosed in European patent application 352,832 as a compound with bronchodilator activity. No activity against the occurrence of heart failure was disclosed, nor the advantages of this specific compound with regard to bioavailability and side-effects.

Related compounds with positive inotropic activity have been disclosed in European patent 158,380. During the development of the most promising compound of European paten 158,380, which is compound II

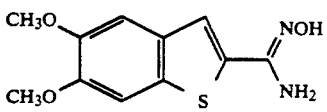

it was found that, when administered orally to conscious restrained dogs the compound consistently produces vomiting and restlessness at doses >10 mg/kg. In clinical Phase I studies, nausea and vomiting were also observed after oral administration of compound II to volunteers, thus restricting the maximum tolerated dose, which may be too low to give a sufficient effect on the prevention of heart failure.

It appeared that the 4-chloro substituted derivative III, disclosed in said European patent 158,380

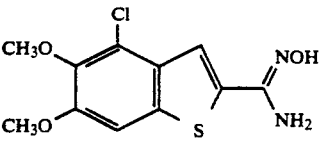

did not cause emesis and vomiting, although restlessness was still observed. However, it also appeared that this improvement with regard to compound II could be fully attributed to its reduced bioavailability. Only modest increases of left ventricular contractility (LV dP/dt) were observed in conscious dogs after oral administration of compound III at doses up to, and including, 50 mg/kg. Poor activity was also observed after oral administration (by gavage) of the compound to anaesthetized cats. Substitution with Cl at the 4-position in the benzothiophene nucleus, thus reduces oral activity. On the ground of these results it was assumed that reduction of vomiting, nausea and restlessness could only be obtained at the expense of bioavailability.

Surprisingly, it has now been found that substitution of the aromatic nucleus with fluorine at the 4-position affords a derivative of formula I that is equipotent to the best known compounds, and nevertheless is devoid of side-effects as vomiting, nausea and restlessness.

When administered orally (by gavage) compounds I and II are approximately equipotent at increasing left ventricular contractility (LV dP/dt), but compound I, after oral administration to conscious dogs, is less emetic than compound II. At an oral dose of compound I (25 mg/kg), which produced marked increases in LV dP/dt, no significant vomiting was observed. The difference in emetic threshold between compounds I and II does not appear to be related to poorer bioavailability of compound I. In multiple dose studies in rats, plasma drug levels were found to be higher after compound I than after an equivalent dose of compound II. On the basis of these results it is anticipated that, in clinical studies, higher doses of compound I cf. compound II may be administered without producing adverse side-effects.

The pharmacological results after oral administration of compounds I (this invention) vs. compounds II and III (EP 158,380), are depicted in table I (cat) and table II (dog).

TABLE I

| | (anaesthetized cat) | |
|---|---|---|
| Compound | active dose (mg/kg) | increase in LV dP/dt (%) |
| I | 15 | 60 |
| II | 10 | 65 |
| III | >50 | 15 |

TABLE II

| | (conscious dog) | | | |
|---|---|---|---|---|
| Compound | dose (mg/kg) | increase in LV dP/dt (%) | emesis | restlessness |
| I | 25 | 45 | 0 | 0 |
| II | 25 | 50–100* | + | + |
| III | 25 | 10 | 0 | + |

*Response too variable to measure accurately. Increase partly due to nausea and restlessness.

Compound I of this invention may be prepared according to the methods described in European patent application 352,832 and in European patent 158,380.

A convenient starting product is aldehyde 1, in which R is hydrogen (J. Med. Chem., 1981, 24, 1395), or R is methyl (J. Org. Chem., 1981, 46, 205, and Synthetic Commun., 1985, 15, 61):

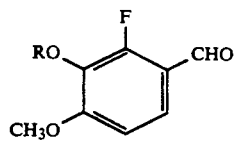

1 R = H or CH₃

This aldehyde was converted into the thiol, and cyclisation was achieved by a two stage process, in which chlorine in carbon tetrachloride was added to the thiol in dioxan to give a dimer, which was treated in a separate reaction with iodine/dioxan, or by a single stage process, in which only iodine/dioxane was used. When R is hydrogen, the hydroxy group was methylated, for instance with iodomethane, after which the esterified carboxylate group was saponified to obtain 4-fluoro-5,6-dimethoxybenzo[b]thiophene-2-carboxylic acid. The resulting reaction steps, i.e. formation of the corresponding 2-nitrile derivative, via the corresponding acid chloride and amide, followed by hydroxylamine treatment to obtain compound I, have been described in the previously mentioned European patent and patent application.

Compound 1 thus obtained, may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, or ascorbic acid. Preferably compound I is isolated as the methanesulphonic acid salt.

The compound of the invention may be administered enterally or parenterally, and for humans preferably orally in a daily dosage of 0,001-10 mg per kg body weight. Mixed with pharmaceutically suitable auxiliaries, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The method of preparation of compound I is further illustrated by the following example.

A. Sodium metal (2 g), cut into small pieces, was added portionwise to a stirred solution of methanol (30 ml) under an atmosphere of nitrogen. When all sodium had dissolved a hot solution of hydroxylamine hydrochloride (6.1 g) in methanol (35 ml) was added. The resultant suspension was stirred for 1 h, then cooled to room temperature and the sodium chloride precipitate was filtered off and washed with methanol. The filtrate was added to 4-fluoro-5,6-dimethoxybenzo[b]-thiophene-2-carbonitrile (7 g) and the mixture was stirred and heated at 40°-50° C. After 1.5 h the mixture was concentrated to 30 ml by vacuum distillation at 30° C. The suspension was diluted with 70 ml of water, stirred, then filtered and the solid was washed with water and dried at 60° C. under vacuum to give 7.75 g of 4-fluoro-N-hydroxy-5,6-dimethoxybenzo[b]thiophene-2-carboximidamide as a pale yellow solid. M.p. 186°-190° C.

B. Methanesulphonic acid (2 ml) was added to a stirred suspension of 7.75 g of 4-fluoro-N-hydroxy-5,6-dimethoxybenzo[b]thiophene-2-carboximidamide in 20 ml of methanol. The starting material dissolved and the resultant solution was filtered dust-free, then concentrated under reduced pressure. Dust-free diethyl ether (20 ml) was then added to the residual oily crystalline residues and the mixture was stirred until a thick paste had formed. More dust-free diethyl ether (30 ml) was then added, the mixture was stirred again, then the solid was filtered and dried at 65° C. under vacuum to give 10 g of pure 4-fluoro-N-hydroxy-5,6-dimethoxybenzo[b]thiophene-2-carboximidamide methanesulphonate. M.p. 190° C. (dec.).

What is claimed is:

1. A method for the treatment of heart failure in a patient, comprising administering the benzo[b]thiophene-2carboximidamide derivative having formula I

or pharmaceutically acceptable salts thereof as a medicament in a therapeutically effective amount that is suitable for the treatment of heart failure, having high bioavailability without inducing nausea, vomiting and/or restlessness.

* * * * *